(12) United States Patent
Mueller (10) Patent No.: US 11,784,031 B2
(45) Date of Patent: Oct. 10, 2023

(54) METHOD OF DETECTING RADICALS USING MASS SPECTROMETRY

(71) Applicant: INFICON, Inc., East Syracuse, NY (US)

(72) Inventor: Norbert Mueller, Gams (CH)

(73) Assignee: INFICON, Inc., East Syracuse, NY (US)

( * ) Notice: Subject to any disclaimer, the term of this patent is extended or adjusted under 35 U.S.C. 154(b) by 0 days.

(21) Appl. No.: 18/017,904

(22) PCT Filed: May 31, 2022

(86) PCT No.: PCT/US2022/031543
§ 371 (c)(1),
(2) Date: Jan. 25, 2023

(87) PCT Pub. No.: WO2022/256295
PCT Pub. Date: Dec. 8, 2022

(65) Prior Publication Data
US 2023/0215711 A1    Jul. 6, 2023

Related U.S. Application Data

(60) Provisional application No. 63/195,277, filed on Jun. 1, 2021.

(51) Int. Cl.
*H01J 49/00* (2006.01)
*H01J 37/32* (2006.01)
*H01J 49/14* (2006.01)

(52) U.S. Cl.
CPC .. *H01J 37/32981* (2013.01); *H01J 37/32009* (2013.01); *H01J 37/3299* (2013.01); *H01J 49/0031* (2013.01); *H01J 49/147* (2013.01)

(58) Field of Classification Search
CPC ........... H01J 37/32981; H01J 37/32009; H01J 37/3299; H01J 49/0031; H01J 49/147
(Continued)

(56) References Cited

U.S. PATENT DOCUMENTS 6,745,095 B1    6/2004  Ben-Dov et al.
9,673,035 B2    6/2017  Park et al.
(Continued)

FOREIGN PATENT DOCUMENTS

WO    2010/093380 A1    8/2010

OTHER PUBLICATIONS

PCT/US2022/031543; filed May 31, 2022; International Search Report and Written Opinion; dated Aug. 16, 2022 (7 pages).

*Primary Examiner* — Kiet T Nguyen
(74) *Attorney, Agent, or Firm* — Barclay Damon LLP (57) ABSTRACT

A method for detecting radicals in process gases in a semiconductor fabrication assembly is provided where the semiconductor fabrication includes a plasma source and a mass spectrometer with an ion source. The method includes separating ions from the process gases and determining a fixed electron energy in which to measure the process gases. Process gases in the semiconductor fabrication assembly are continuously sampled. A first measurement is performed on the sampled process gases at the electron energy using the mass spectrometer, where the first measurement is performed with the plasma source off. A second measurement of the sampled process gases is performed at the fixed electron energy using the mass spectrometer, where the second measurement is performed with the plasma source on. An amount of a radical present in the sampled process gases is determined as a difference between the second measurement and the first measurement.

11 Claims, 6 Drawing Sheets

(58) Field of Classification Search
USPC .......................................................... 250/282
See application file for complete search history.

(56) References Cited

U.S. PATENT DOCUMENTS

2004/0000647 A1     1/2004  Horsky
2008/0009099 A1     1/2008  Kishkovich et al.
2022/0196597 A1*    6/2022  Yang ........................ H01J 49/10
2022/0392812 A1*    12/2022 Moalem ............ H01J 37/32899

* cited by examiner

610 — Connect a mass spectrometer with an electron impact ion source to the semiconductor fabrication system such that process gases from the semiconductor fabrication system can enter the mass spectrometer.

612 — Continuously sample and measure the process gas using the mass spectrometer.

614 — The measuring of the process gas comprises performing measurements at a fixed electron energy of the intensity on the mass number of the radical to be detected when the plasma is off.

616 — The measuring of the process gas comprises performing measurements at a fixed electron energy of the intensity on the mass number of the radical to be detected when the plasma is on.

618 — Determine the number of radicals by evaluating the difference between the plasma on measurement and the plasma off measurement.

METHOD OF DETECTING RADICALS USING MASS SPECTROMETRY

CROSS-REFERENCE TO RELATED APPLICATIONS/PRIORITY CLAIM

This application is a national stage application pursuant to 35 U.S.C. § 371 of International Application No. PCT/US2022/031543, filed on May 31, 2022, which claims the benefit of the filing date and the priority of U.S. Provisional Patent Application No. 63/195,277, filed Jun. 1, 2021. The entire contents of said applications are hereby incorporated by reference.

TECHNOLOGICAL FIELD

This disclosure relates generally to the field of semiconductor/microelectronics fabrication and more specifically to a method of detecting radicals during the semiconductor/microelectronics fabrication process using mass spectrometry.

BACKGROUND

Semiconductors are an important component used in the production of many different types of consumer and industrial products. An important part of the semiconductor manufacturing process is the etching process of the semiconductor wafer, which is typically done using plasma processing (i.e., using a plasma). The etching, especially the etching of extremely thin layers of semiconductor material (e.g., semiconductors with structures that are ≤5 nm in size) is efficiently performed using radicals. Radicals are uncharged molecules that have an unpaired valence electron and are therefore, highly reactive and short-lived. Their high chemical reactivity with the surface of the wafer leads to the removal of atoms from the wafer and wafer etching. These radicals, together with positive and negative ions, are created in the plasma. As the negative ions have a detrimental influence on the etching process, they are separated using electrical fields so they do not reach the semiconductor wafer. Determining the amount or number of radicals in present in a semiconductor fabrication assembly/system is difficult to do. However, knowing the amount of radicals in the assembly/system is beneficial as it can enable one to better calculate/predict the etch rate on the wafer. In other words, the higher the amount of radicals, the higher the wafer etch rate. Conversely, the lower the amount of radicals, the lower the wafer etch rate.

The creation of radicals in the plasma and the etch rate on the wafer is assumed to be relatively stable, however the radical density may change if is there is a power drift on the plasma source. In addition, electric fields produced by electric potentials being applied to grids are used in semiconductor fabrication assemblies/systems to reject ions while allowing neutral particles and radicals to pass. These are sometimes referred to as filters. As the ions and the radicals attack the grids, they wear out, become non-conductive, or even may change their electrical characteristics. All of this can lead to a loss of filter efficiency for the positive and/or negative ions, which results in a change in the density of ions, neutrals, and radicals on the wafer (i.e., a change in the etch rate). Moreover, an unexpected change in the amount of process gases supplied to the process chamber can also influence the etch rate and produce unreliable results on the etched wafer. Currently, test wafers are inserted into the process chamber from time to time in order to test the reaction of the radicals on the test wafer. This enable adjustment of process variables/parameters to achieve the optimum conditions for the production wafers (non-test wafers). For example, frequency of the power to create the plasma, pressure of one or more process gases or the composition of the gas inside the plasma chamber can be changed to account for the level of radicals present in the system. However, the use of test wafers does not provide continuous information on the status of the plasma and the number of radicals present. As a result, the etch rate on the wafer is changing, which results in poor wafer reproducibility and/or a poor wafer quality.

These are just some of the problems associated with the methods of detecting radicals during semiconductor/microelectronics fabrication that are currently employed.

SUMMARY

An embodiment of the inventive method uses a mass spectrometer with an electron impact ion source that allows for operation at low and variable electron energies enabling "appearance potential" measurements to be performed on the process gases in the process chamber. Ionized radicals and ions from the process gases in the process chamber in the ground state are detected on identical mass numbers in the mass spectrum. However, when the process gases are measured at low electron energies, the radicals that are present will be ionized at a much higher rate than the neutral gas components. The number of a particular radical is determined by the difference between the measurement at the low electron energy (e.g., below 40 eV) and the appearance potential.

The inventive method measures the current produced by ions landing on a Faraday detector or alternatively the current produced by a Secondary Electron Multiplier on which the ions land, which is often referred to as the intensity. As such, the inventive method measures the intensity on the mass on the mass number of the desired radical at a fixed electron energy under plasma off conditions and then under plasma on conditions. This results in a small data set which is easier to evaluate on-line than a data set resulting from creating a constantly increasing electron energy in the ion source of the mass spectrometer while measuring the intensity on select mass number under plasma-off and plasma-on conditions. The small data set can therefore provide better real time information so that adjustments to the fabrication process can be performed, which results in a better finished product.

In an embodiment, a method for detecting radicals using a mass spectrometer is provided. The method comprises the steps of: (1) separating the ions from the neutral particles and radicals present in the process gases; (2) performing a first measurement of the process gases using the mass spectrometer while the plasma source of the semiconductor fabricating assembly is off; (3) performing a second measurement of the process gases using the mass spectrometer while the plasma source of the semiconductor fabricating assembly is on; and (4) determining the amount of radicals present at a certain electron energy by taking the difference between the second measurement and the first measurement.

The steps described above can be performed continuously during the operation of the semiconductor fabricating assembly. In an embodiment, the method may first be performed at a range of electron energies to determine the optimum electron energy that produces a large differentiation between the neutral particles and the radicals. This electron energy is then set as the fixed electron energy in which to perform continuous measurements of the process gases using the mass spectrometer.

Another embodiment of the method for detecting radicals in process gases during semiconductor fabrication using a mass spectrometer with an ion source includes separating ions from the process gases and determining a fixed electron energy in which to measure the process gases. The process gases in the semiconductor fabrication assembly are continuously sampled. A first measurement of the sampled process gases in the semiconductor fabrication assembly is performed at the fixed electron energy using the mass spectrometer, wherein the first measurement is performed with the plasma source off. A second measurement of the sampled process gases in the semiconductor fabrication assembly is performed at the fixed electron energy using the mass spectrometer, wherein the second measurement is performed with the plasma source on. An amount of a radical present in the sampled process gases is determined as a difference between the second measurement and the first measurement.

In an embodiment, determining the fixed electron energy comprises performing a plurality of measurements of the sampled process gases in the semiconductor fabrication assembly over a range of electron energies with the plasma source off. Another plurality of measurements of the sampled process gases in the semiconductor fabrication assembly is performed over a range of electron energies with the plasma source on. An electron energy is determined for the radical where the difference between the measurement with the plasma source on and the measurement with the plasma source off is the greatest and setting the determined electron energy as the fixed electron energy.

In an embodiment, the method of detecting radicals using a mass spectrometer further includes performing a third measurement of the sampled process gases in the semiconductor fabrication assembly at a second, different fixed electron energy using the mass spectrometer, wherein the third measurement is performed with the plasma source off. A fourth measurement of the sampled process gases in the semiconductor fabrication assembly is performed at the second electron energy using the mass spectrometer, wherein the second measurement is performed with the plasma source on. An amount of a second radical present in the sampled process gases is determined as a difference between the fourth measurement and the third measurement, wherein the second electron energy is different than the first electron energy.

BRIEF DESCRIPTION OF DRAWINGS

A more particular description of the invention briefly summarized above may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. Thus, for further understanding of the nature and objects of the invention, references can be made to the following detailed description, read in connection with the drawings in which.

The purpose of these drawings is to depict salient features of the method of detecting radicals using mass spectrometry and are not specifically provided to scale.

DETAILED DESCRIPTION

The following discussion relates to various embodiments of a the method of detecting radicals using mass spectrometry and are not specifically provided to scale. It will be understood that the herein described versions are examples that embody certain inventive concepts as detailed herein. To that end, other variations and modifications will be readily apparent to those of sufficient skill. In addition, certain terms are used throughout this discussion in order to provide a suitable frame of reference with regard to the accompanying drawings. These terms such as "first", "second" and the like are not intended to limit these concepts, except where so specifically indicated. The terms "about" or "approximately" as may be used herein may refer to a range of 80%-125% of the claimed or disclosed value.

Figure 1:
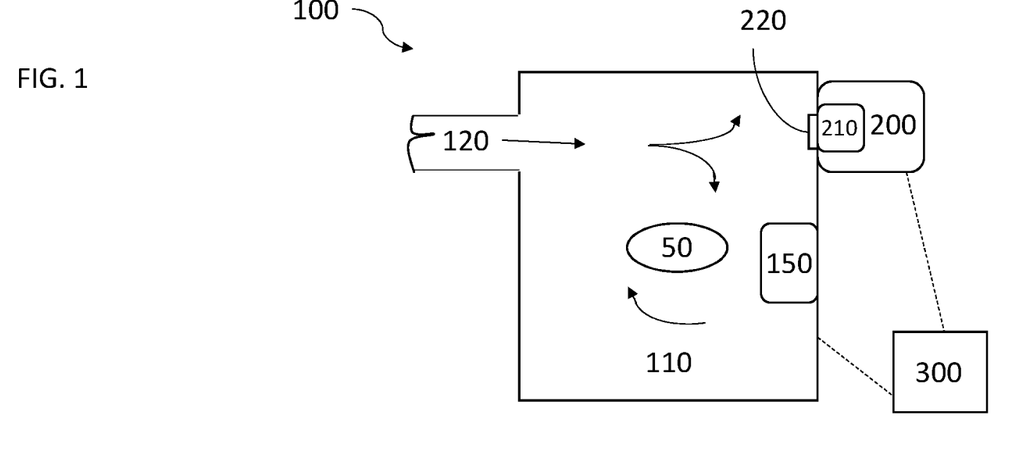
FIG. 1 schematically illustrates an embodiment of a process chamber of a semiconductor fabrication assembly with a mass spectrometer.

FIG. 1 schematically illustrates an example of a portion of a semiconductor fabricating assembly 100 including a process chamber 110 that is configured to accept a semiconductor wafer 50 and a process gas outlet 120 that delivers process gases into the process chamber 110. The plasma source is shown with reference number 150, however in other embodiments the plasma source 150 may positioned differently that what is shown in FIG. 1. A mass spectrometer 200 is connected to the semiconductor fabricating assembly 100. As shown, the mass spectrometer 200 is connected to the process chamber 110 through a gas-tight connection so that process gases in the process chamber 110 can enter the ion source 210 of the mass spectrometer 200. A pressure reduction stage 220 is further included, which can include at least one valve that reduces the (high) pressure in the plasma 110 to the (mower) operating pressure of the ion source 210 and the mass spectrometer 200. The pressure range in the plasma 110 may vary from 5.0E-3 mbar up to several mbar. The pressure in the ions source 210 and the mass spectrometer 200 are may be from 1.0E6 to 1.0E-5 mbar.

As shown in FIG. 1, the mass spectrometer 200 is in communication with a controller 300, which may be configured to control operating parameters of the mass spectrometer 200, enable adjustment of said parameters, as well as receive and display measurement data from the mass spectrometer 200. In another embodiment, the controller 300 may be further configured to be in communication with the semiconductor fabrication assembly 100 and may be configured to control operating parameters of the semiconductor fabrication process as well as enable adjustment of said operating parameters. The controller 300 may include one or more processors, a memory, a user input interface and a graphical output interface (GUI).

Figure 2:
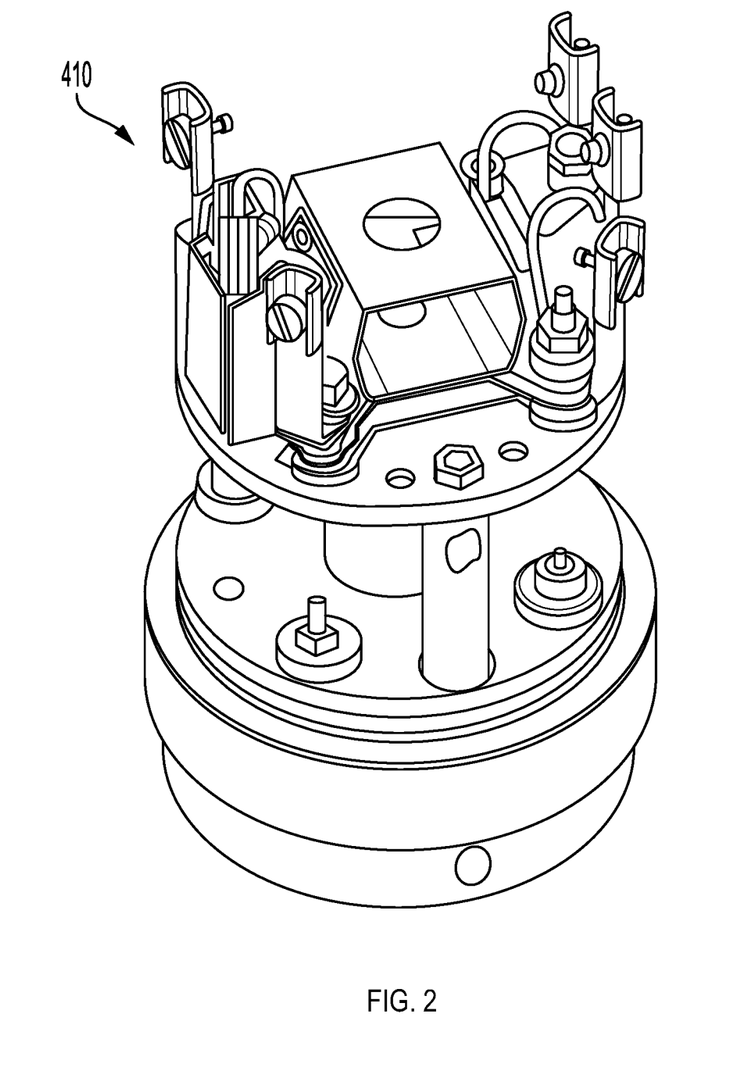
FIG. 2 illustrates an example of steps that may be employed when implementing an embodiment of detecting radicals using mass spectrometry.
Figure 3:
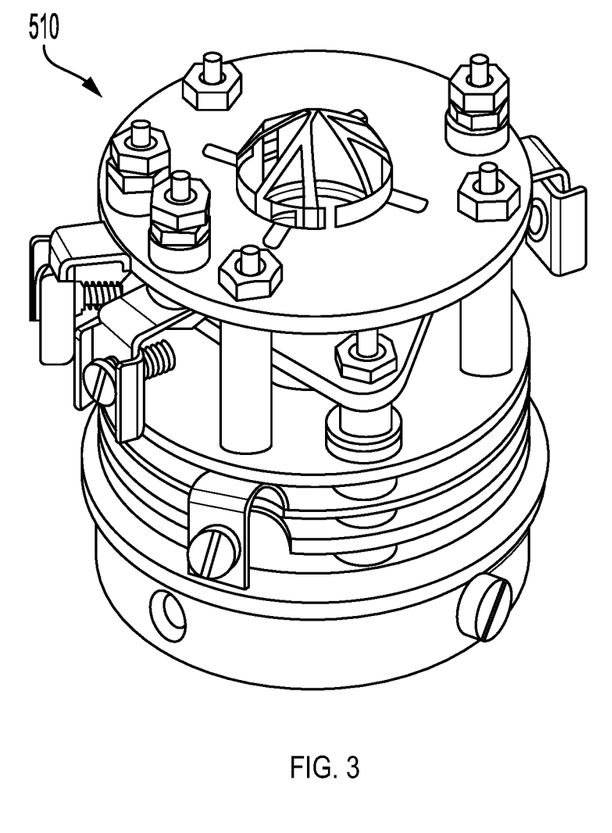
FIG. 3 illustrates an example of an appearance potential measurement overlayed on an example of a measurement taken at low electron energies, specifically at 31 eV.

The ion source 210 of the mass spectrometer can generally be any type of ion source. Referring to FIG. 2, an example of an Open Cross Beam ion source 410 is shown for a high performance spectrometer. A benefit of this ion source 410 is that it has an open configuration which allows process gases to easily move into the ion source 410. FIG. 3 shows an example of an Open High Sensitivity ion source 510 for a standard residual gas analyzer. This ion source 510 does not have a completely open configuration so it is more difficult for process gases to move into the ion source 510. The electron energies in both ion sources 410, 510 are adjustable from 10 eV to 100 eV. Both of these ion sources 410, 510 provide a direct path for the radicals to be measured that are generated by the plasma to enter the sensitive region of the ion source without hitting other parts of the process chamber 110 or the mass spectrometer 200. This is important when measuring the level of radicals since the radicals can change state if they strike a wall or surface inside the process chamber 110 or the mass spectrometer 200. For example, the radical may no longer be in an excited state, and therefore no longer be a radical.

Figure 4:
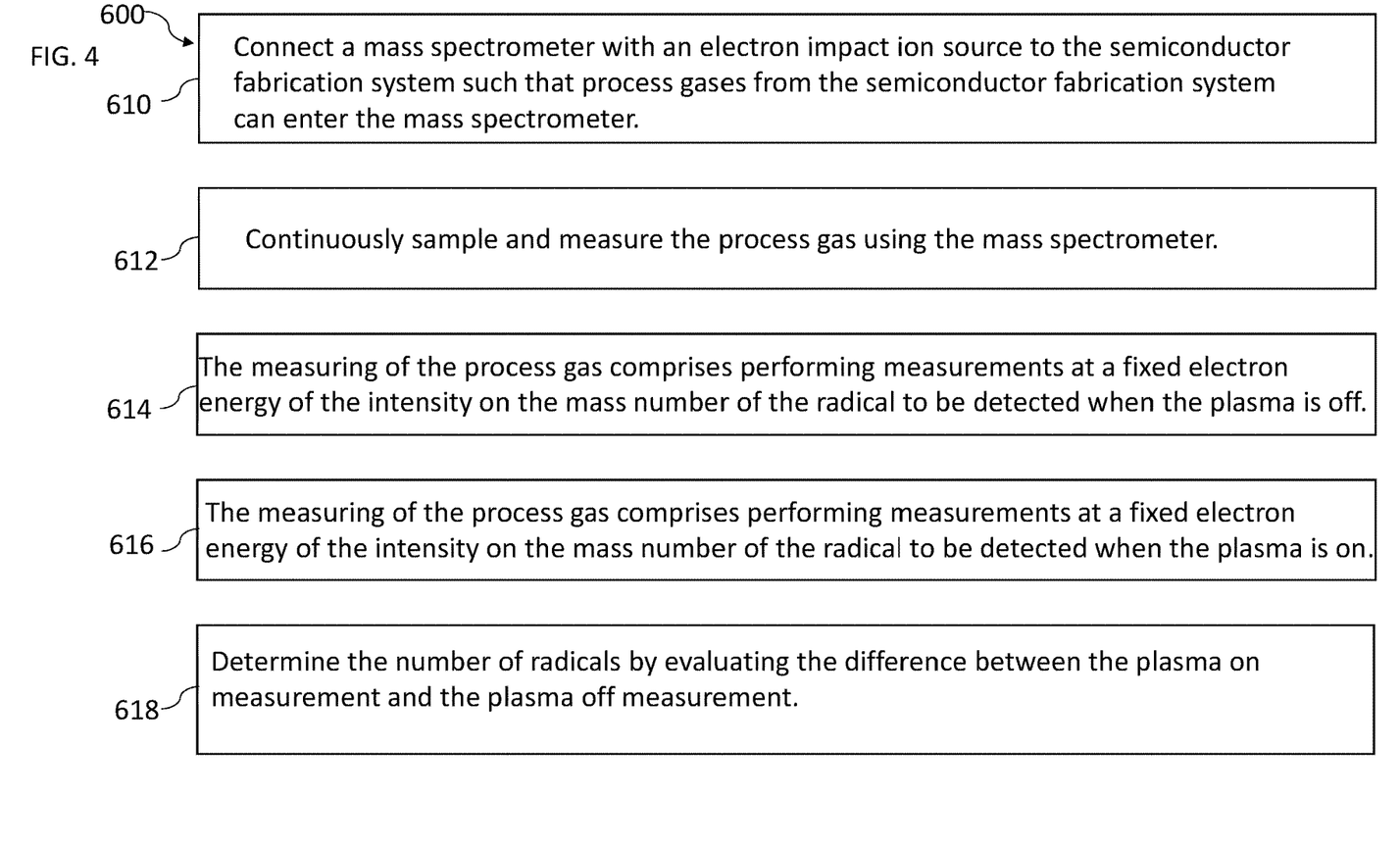
FIG. 4 illustrates an example of an ion source that can be used to perform the disclosed method.

A method 600 of detecting radicals will not be described with reference to FIG. 4. In step 610, a mass spectrometer 200 (FIG. 1) with an electron impact ion source is connected to the semiconductor fabrication system 100 (FIG. 1). The connection between the mass spectrometer 200 (FIG. 1) and the semiconductor fabrication system 100 (FIG. 1) is a gas-tight connection which enables process gasses from the semiconductor fabrication system 100 (FIG. 1) can enter the mass spectrometer 200 (FIG. 1), and specifically the ion source 210 (FIG. 1) of the mass spectrometer 200 (FIG. 1). In step 615, the ions are prevented from reaching the mass spectrometer 200 (FIG. 1) by using one or more electric fields, such as filters. As previously discussed the filters may be one or more grids that have an applied electric potential. The mass spectrometer 200 (FIG. 1) continuously samples and measures the process gases in the semiconductor fabrication system 100 (FIG. 1). In the embodiment shown in FIG. 1, the mass spectrometer 200 measures the process gases from the process chamber 110 of the semiconductor fabrication system 100.

The measuring process of step 612 is further detailed in steps 614 and 616. First in step 614, a measurement of the gases in the semiconductor fabrication assembly 100 (FIG. 1) is performed with the plasma source off or in a plasma-off condition. Ionized radicals and neutral particles from the process gases in the process chamber in the ground state are detected on identical mass numbers in the mass spectrum. The measurement is taken at a fixed electron energy and measures the intensity of the peak at a given mass number associated with the desired radical to be detected. Next in step 616, another measurement of the process gases is performed with the plasma source on or in a plasma-on condition. When the plasma source is on, the process gases are measured again at the same fixed or set electron energy and the radicals that are present are ionized at a much higher rate than the neutral gas components. In step 618, the number/amount of radicals can be determined at the fixed electron energy by determining the difference between the measurements of step 616 and 614.

Figure 5:
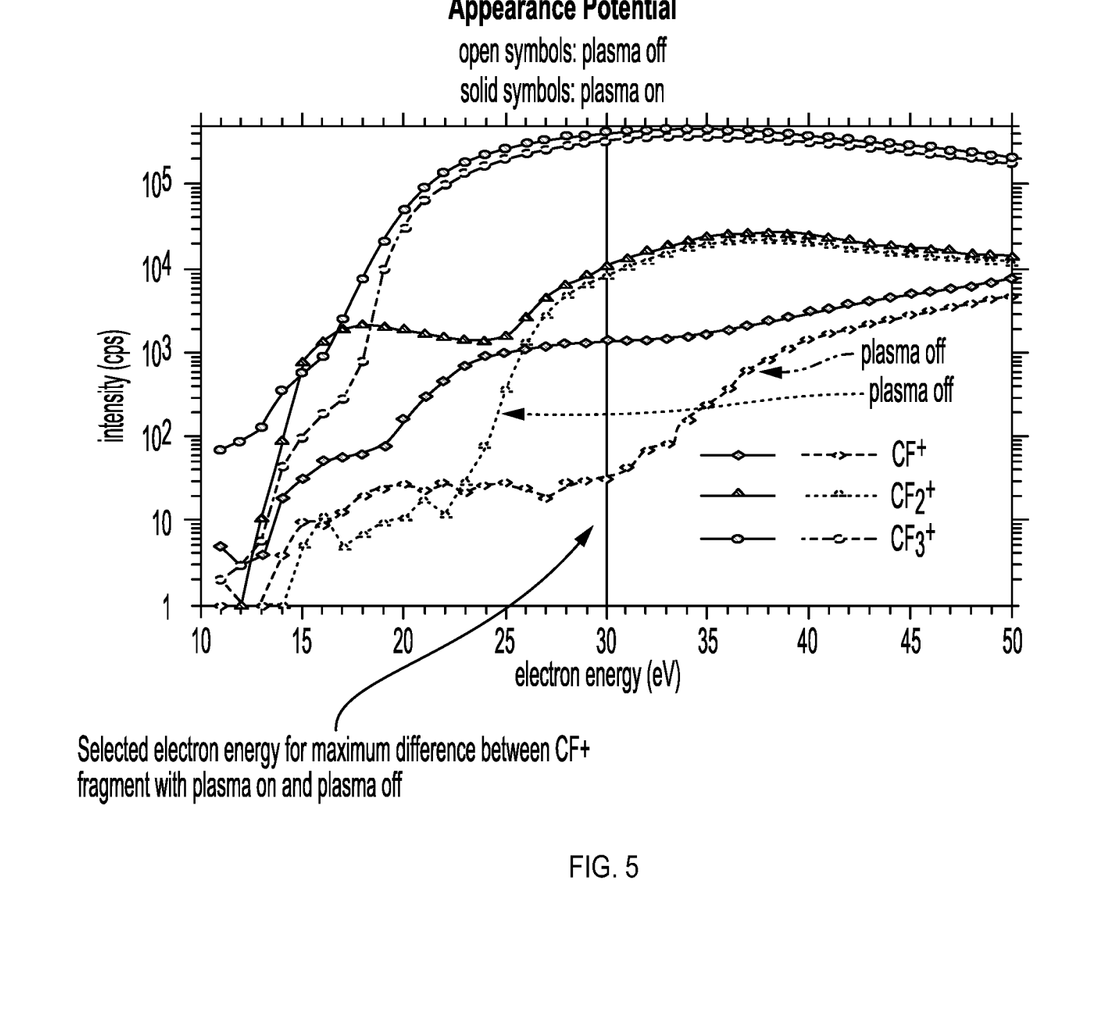
FIG. 5 illustrates another embodiment of an ion source that can be used to perform the disclosed method.

An example of the measurement data produced by the mass spectrometer 200 (FIG. 1) and displayed by the controller 300 (FIG. 1) is shown in FIG. 5. In this example, the plasma source 150 (FIG. 1) that was used had carbon tetrafluoride ($CF_4$) gas introduced into the plasma chamber. However, other embodiments may use other gases such as Hydrogen or $NF_3$, in which case there will be different radicals emitted from the plasma source. Accordingly, the measurements were taken at 30 eV, correspond to the electron energy (31 eV) where the difference between the plasma-on and plasma-off measurements are the greatest for the $CF^+$ radical. As shown, three different radicals of $CF_4$ are present ($CF^+$, $CF_2^+$, $CF_3^+$). Each radical produces a different value as can be seen in FIG. 5. A first measurement is taken in a plasma-off condition as is shown by the values having open symbols. Next, a measurement is taken in the plasma-on condition as is shown by the values having solid symbols. As can be seen, there is large difference between the plasma-off and plasma-on measurements for the $CF^+$ as compared to the other radicals ($CF_2^+$, $CF_3^+$). Subsequent measurements can then be taken at lower electron energies (eV) to better separate the plasma-off and plasma-on measurements of the other radicals in order to more easily determine the amount of each radical in the sample as a difference between the plasma-on and plasma-off values. Continuous measuring can then take place in the plasma-off and plasma-on states at the electron energy determined to result in the greatest differentiation between the plasma-on measurement and the plasma-off measurement for the given radical. For example, the continuous measurements for $CF^+$ would take place at 31 eV.

Figure 6:
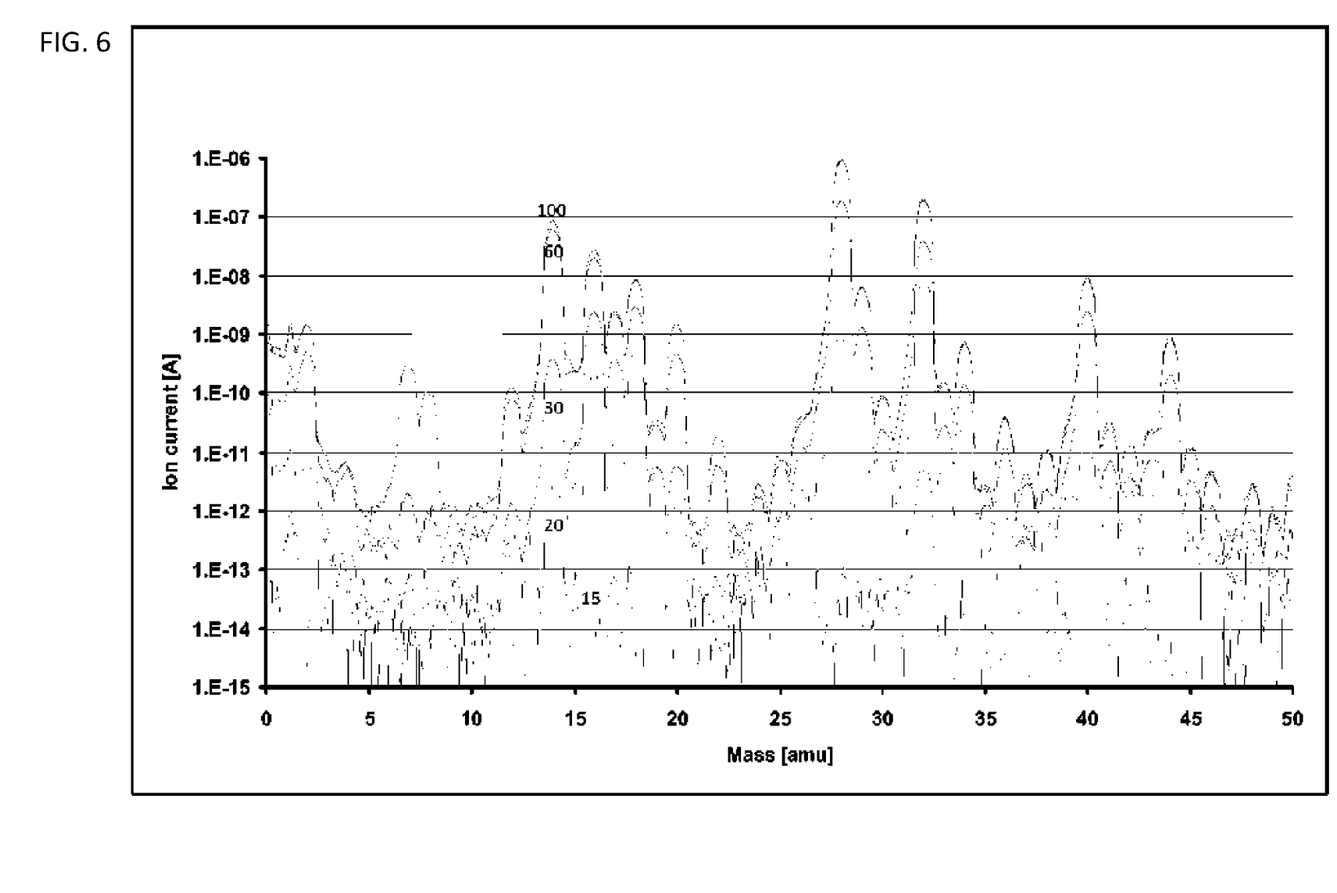
FIG. 6 illustrates a measurement done by an Open High-Sensitivity (HS) mass spectrometer on air over the entire mass range of the mass spectrometer and at varying electron energies.

Referring to FIG. 6 represents a graph of air introduced in to the Open High Sensitivity (HS) ion source 510. The curves represent a scan of the entire mass range of the mass spectrometer at varying electron energies. Compared to FIG. 5, which only shows the intensity at mass number 31. FIG. 6 shows the entire gas composition of what is introduced into the mass spectrometer 200 (FIG. 1) at different electron energies. For example, mass number 28 m/e refers to nitrogen ($N_2$) and it can be seen that the intensity of the curve is lower at lower electron energies.

While the present invention has been particularly shown and described with reference to certain exemplary embodiments, it will be understood by one skilled in the art that various changes in detail may be effected therein without departing from the spirit and scope of the invention that can be supported by the written description and drawings. Further, where exemplary embodiments are described with reference to a certain number of elements, it will be understood that the exemplary embodiments can be practiced utilizing either less than or more than the certain number of elements.

The invention claimed is:

1. A method for detecting radicals in process gases during semiconductor fabrication having a plasma source and a mass spectrometer with an ion source, the method comprising:
   separating ions from the process gases;
   determining a fixed electron energy in which to measure the process gases;
   continuously sampling process gases in a semiconductor fabrication assembly;
   performing a first measurement of the sampled process gases in the semiconductor fabrication assembly at the fixed electron energy using the mass spectrometer, wherein the first measurement is performed with the plasma source off;
   performing a second measurement of the sampled process gases in the semiconductor fabrication assembly at the fixed electron energy using the mass spectrometer, wherein the second measurement is performed with the plasma source on;
   determining an amount of a radical present in the sampled process gases as a difference between the second measurement and the first measurement.

2. The method of claim 1, wherein determining the fixed electron energy comprises:
- performing a plurality of measurements of the sampled process gases in the semiconductor fabrication assembly over a range of electron energies with the plasma source off;
- performing a plurality of measurements of the sampled process gases in the semiconductor fabrication assembly over a range of electron energies with the plasma source on;
- determining an electron energy for the radical where a difference between a measurement with the plasma source on and a measurement with the plasma source off is greatest; and
- setting the determined electron energy as the fixed electron energy.

3. The method of claim 2, further comprising adjusting one or more semiconductor manufacturing process variables according to the determined amount of the radical detected in the sampled process gases.

4. The method of claim 1, further comprising structuring the ion source to connect to the semiconductor fabrication assembly via a gas-tight connection.

5. The method of claim 1, wherein the first and second measurement data are output to a controller and displayed on a graphical user interface.

6. The method of claim 1, wherein the ion source is an electron impact ion source.

7. A method for detecting radicals in process gases of a semiconductor fabrication assembly having a plasma source, the method comprising:
- structuring a mass spectrometer with an ion source to connect to the semiconductor fabrication assembly via a gas-tight connection;
- removing ions from the process gases;
- determining a set electron energy in which to measure the process gases;
- continuously sampling process gasses in the semiconductor fabrication assembly;
- performing a first measurement of the sampled process gases in the semiconductor fabrication assembly at the set electron energy using the mass spectrometer, wherein the first measurement is performed with the plasma source off;
- performing a second measurement of the sampled process gases in the semiconductor fabrication assembly at the set electron energy using the mass spectrometer, wherein the second measurement is performed with the plasma source on;
- determining an amount of a radical present in the sampled process gases as a difference between the second measurement and the first measurement.

8. The method of claim 7, wherein determining the set electron energy comprises:
- performing a plurality of measurements of the sampled process gases in the semiconductor fabrication assembly over a range of electron energies with the plasma source off;
- performing a plurality of measurements of the sampled process gases in the semiconductor fabrication assembly over a range of electron energies with the plasma source on;
- determining an electron energy for the radical where a difference between a measurement with the plasma source on and a measurement with the plasma source off is greatest; and
- setting the determined electron energy as the set electron energy.

9. The method of claim 7, further comprising adjusting one or more semiconductor manufacturing process variables according to the amount of the radical detected in the sampled process gases.

10. The method of claim 7, wherein the first and second measurement data are output to a controller and displayed on a graphical user interface.

11. The method of claim 7, wherein the ion source is an electron impact ion source.

* * * * *